United States Patent [19]

Schwindeman

[11] Patent Number: 4,836,845

[45] Date of Patent: * Jun. 6, 1989

[54] HERBICIDALLY ACTIVE ISOXAZOLYL-IMADAZOLIDINONE DERIVATIVES

[75] Inventor: James A. Schwindeman, Akron, Ohio

[73] Assignee: American Cyanamid Company, Stamford, Conn.

[*] Notice: The portion of the term of this patent subsequent to Nov. 17, 2004 has been disclaimed.

[21] Appl. No.: 95,791

[22] Filed: Sep. 14, 1987

Related U.S. Application Data

[63] Continuation-in-part of Ser. No. 744,728, Jun. 14, 1985, Pat. No. 4,707,180.

[51] Int. Cl.$^4$ .................... A01N 43/80; C07D 261/14
[52] U.S. Cl. ........................................ 71/92; 548/245; 548/246
[58] Field of Search .................... 71/92; 548/245, 246, 548/317, 318

[56] References Cited

U.S. PATENT DOCUMENTS 4,707,180 11/1987 Schwindeman .................. 71/92
4,756,744 7/1988 Schwindeman .................. 71/92

Primary Examiner—Donald G. Daus
Assistant Examiner—E. Bernhardt
Attorney, Agent, or Firm—Alice C. Brennan

[57] ABSTRACT

The invention relates to certain 3-isoxazolyl-2-imidazolidinone derivatives, namely 3-[5- or 3-substituted-3- or -5-isoxazolyl]-1-substituted-4- or 5-substituted amino-2-imidazolidinones and the use thereof for preemergence or postemergence control of noxious plants, i.e., weeds.

6 Claims, No Drawings

HERBICIDALLY ACTIVE ISOXAZOLYL-IMADAZOLIDINONE DERIVATIVES

CROSS REFERENCE TO RELATED APPLICATION

This application is a continuation-in-part of copending application Ser. No. 744,728 filed June 14, 1985 now U.S. Pat. No. 4,707,180.

FIELD OF THE INVENTION

This invention relates to certain 3-isoxazolyl-2-imidazolidinone derivatives, namely 3-[5- or 3-substituted-3- or -5-isoxazolyl-1-substituted-4- or 5- substituted amino-2-imidazolidinones and the use thereof for pre-emergence or postemergence control of noxious plants, i.e., weeds.

DESCRIPTION OF THE INVENTION

This invention provides herbicidally active 3-[5- or 3-substituted- 3- or -5-isoxazolyl]-1-substituted-4-or 5 -substituted amino-2-imidazolidinones represented by the Formula I:

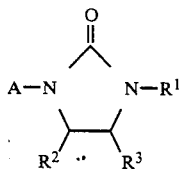

wherein A is

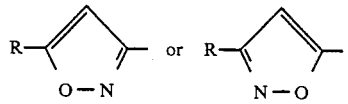

Wherein:

R is up to $C_6$ alkyl, haloalkyl or cycloalkyl, up to $C_5$ alkenyl or alkynyl; $-R^4-O-R^5$ or $-R^4-S-R^5$ wherein $R^4$ is up to $C_6$ alkylene and $R^5$ is up to $C_6$ alkyl or optionally substituted phenyl or benzyl;

$R^1$ is up to $C_3$ alkyl or allyl;

$R^2$ and $R^3$ are selected from hydrogen, hydroxy or $-NR^6R^7$ with the proviso that one of $R^2$ or $R^3$ must $-NR^6R^7$, wherein $R^6$ is selected from hydrogen or up to $C_6$ alkyl or haloalkyl; and $R^7$ is

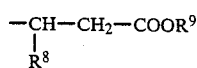

wherein $R^8$ is selected from hydrogen, up to $C_6$ alkyl or haloalkyl, aryl or substituted aryl; and $R^9$ is selected from alkali metal, hydrogen, up to $C_6$ alkyl, haloalkyl or alkoxyalkyl, phenyl or substituted phenyl.

Preferred compounds are those wherein $R^1$ is $C_1$ to $C_3$ alkyl, $R^3$ is hydrogen, $R^2$ is $R^6$-N-CH($R^8$)-CH$_2$COOR$^9$ wherein $R^8$ is hydrogen or $C_1$ to $C_3$ alkyl, $R^9$ is hydrogen or $C_1$ to $C_3$ alkyl and A is

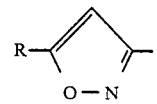

wherein R is $C_1$ to $C_3$ alkyl.

The compounds of this invention can be synthesized using available starting materials, such as the isoxazolyl-imidazolidinone compounds described in U.S. Pat. No. 4,268,679 and using techniques known to the art. For example, certain of the compounds of this invention may be prepared by reacting an isoxazolyl-imidazolidinone compound of the formula:

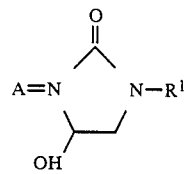

wherein A and $R^1$ are as previously defined, with a suitably substituted amine of the formula, $NHR^6R^7$, wherein $R^6$ and $R^7$ are as previously defined. The reaction is typically conducted in an inert organic solvent medium at up to reflux temperature and usually in the presence of a strong mineral or organic acid, e.g., p-toluenesulfonic acid.

The following Examples are illustrative of the preparation of certain compounds of this invention.

EXAMPLE I

Preparation of: 3-[5-(t-butyl)-3-isoxazolyl]-1-methyl-4-[N-(2-carboethoxy) ethyl]amino-2-imidazolidinone.

To a 100 milliliter flask provided with a magnetic stirring bar, Dean-Stark trap and a reflux condenser were charged 2.87 grams (0.012 mole) of 3[5-(t-butyl)-3-isoxazolyl]-1-methyl-4-hydroxy-2imidazolidinone, 30 milliliters of dry toluene, 3.70 grams (0.0316 mole) of 2-(carboethyoxy)ethyl amine and 0.20 gram of p-toluenesulfonic acid. The reaction mixture was stirred vigorously for 30 minutes at room temperature then heated about 70° C. for about one hour. The reaction mixture was then heated to reflux and maintained at reflux until HPLC analysis indicated complete conversion of starting materials. The reaction mixture was then cooled, transferred to a separatory funnel, diluted with 100 milliliters of ethyl acetate and washed with 100 milliliters of saturated aqueous sodium bicarbonate. The organic layer was drawn-off and reserved and the aqueous layer was back extracted with 2×100 milliliter portions of ethyl acetate. The combined organic layers were dried over anhydrous magnesium sulfate, filtered and concentrated in vacuo affording 4.51 grams of golden oil confirmed by NMR and MS analyses as the desired product.

EXAMPLE II

Preparation of: 3-[5-(t-butyl)-3-isoxazolyl]-1-methyl-4-[N(2-carbomethoxy)ethyl]amino-2-imidazolidinone.

To a 100 milliliter flask provided with a magnetic stirring bar, a Dean-Stark trap and a reflux condenser were charged 3.37 grams (0.0141 mole) of 3-[5-(t-butyl)-3-isoxazolyl]-1-methyl-4-hydroxy-2imidazolidinone, 35 milliliters of dry toluene and 0.25 gram of p-toluenesulfonic acid. To this tan colored suspension were added 3.63 grams (0.0352 mole) of 2-(carbomethoxy)ethyl amine resulting in an orange colored solution. The reaction mixture was heated to reflux and maintained at reflux until TLC analysis indicated substantial consumption of starting material. The reaction mixture was cooled and transferred to a separatory funnel containing 100 milliliters of ethyl acetate and 100 milliliters of saturated aqueous sodium bicarbonate. The aqueous layer was drawn-off and back extracted with 3×100 milliliter portions of ethyl acetate. The combined organic layers were dried over anhydrous magnesium sulfate, filtered and concentrated in vacuo affording 4.57 grams of a yellow oil confirmed by NMR analysis as the desired product.

EXAMPLE III

Preparation of: 3-[5-(t-butyl)-3-isoxazolyl]-1-methyl-4-[N-(2-carboxy)ethyl]amino-2-imidazolidinone.

To a 100 milliliter flask provided with a magnetic stirring bar and fitted with a stopper were charged 2.00 grams (0.0059 mole) of 3-[5-(t-butyl)-3-isoxazolyl]-1-methyl-4-[N-(2-carbethoxy)ethyl]amino-2-imidazolidinone, prepared as described in Example I, and 15 milliliters of ethanol. The resulting yellow solution was treated with 0.47 grams of 85.6% assay potassium hydroxide and 3 milliliters of water. The reaction mixture was stirred for about two hours at room temperature after which time TLC analysis indicated complete consumption of starting materials. The reaction mixture was concentrated on a rotary evaporator and the residue was dissolved in 70 milliliters of water and transferred to a separatory funnel, wherein it was acidified to pH 5.0 with 5% aqueous hydrochloric acid and extracted with 4×100 milliliter portions of ethyl acetate. The combined organic extracts were dried over anhydrous magnesium sulfate, filtered and concentrated in vacuo affording 1.74 grams of tan solid confirmed by NMR and MS analyses as the desired product.

EXAMPLE IV

Preparation of: 3-[5-(t-butyl)-3-isoxazolyl]-1-methyl-4-[N-(2-carboethoxy-1-methyl)ethyl]amino-2-imidazolidinone.

To a 200 milliliter flask provided with a Dean-Stark trap, a magnetic stirring bar and a reflux condenser were charged 7.15 grams (0.0278 mole) of 93% assay 3-[5-(t-butyl)-3-isoxazolyl]-1-methyl-4-hydroxy-2-imidazolidinone, 75 milliliters of toluene and 0.60 grams of p-toluenesulfonic acid. To this stirred mixture were added 8.00 grams (0.061 mole) of 2-carboethoxy-1-methyl amine resulting in a tan colored, homogeneous solution. The reaction mixture was heated to reflux and maintained at reflux until HPLC analysis indicated complete consumption of starting materials, an additional 2.0 grams of 2-carboethoxy-1-methyl amine having been added during the course of refluxing. The reaction mixture was then cooled, diluted with 100 milliliters of toluene, transferred to a separatory funnel and washed successively with 200 milliliter portions of saturated aqueous sodium bicarbonate solution, water and saturated aqueous sodium chloride solution. The organic layer was isolated and dried over anhydrous magnesium sulfate, filtered and concentrated in vacuo affording 11.87 grams of orange oil. The oil was purified by column chromatography on silica gel using 9:1 v/v ethyl acetate:hexane as an eluent, affording 10.53 grams of purified material confirmed by NMR, IR and MS analyses as the desired product.

EXAMPLE V

Preparation of: 3-[5-(t-butyl)-3-isoxazolyl]-1-methyl-4-[N-(2-carboxy-1-methyl)ethyl]amino-2-imidazolidinone.

To a 100 milliliter flask provided with a magnetic stirring bar and fitted with a stopper were charged 3.30 grams (0.0094 mole) of 3-[5-(t-butyl)-3-isoxazolyl]-1-methyl-4-[N-(2-carboethoxy-1-methyl)ethyl]amino-2-imidazolidinone, prepared as described in Example IV, 15 milliliters of ethanol and 5 milliliters of water. To the resulting orange colored homogenous solution was added 0.79 gram of 85.6% assay potassium hydroxide. After stirring for about 3 hours at room temperature, the reaction mixture was concentrated in vacuo affording an orange colored semi-solid residue. The residue was dissolved in 150 milliliters of water, transferred to a separatory funnel and washed with 120 milliliters of diethyl ether. The aqueous layer was drawn-off, acidified to about pH 5.0 with 5% aqueous hydrochloric acid and extracted with 4×150 milliliter portions of ethyl acetate. The combined ethyl acetate extracts were dried over anhydrous magnesium sulfate, filtered and concentrated in vacuo affording 2.82 grams of a tan colored foam confirmed by NMR and MS analyses as the desired product.

Although the invention has been illustrated by the foregoing Examples with regard to the preparation of certain compounds within the scope of Formula I, it is to be understood that other compounds within the scope of Formula I may readily be prepared by those skilled in the art simply by varying the choice of starting materials and using the same or similar techniques.

Weed control in accordance with this invention is effected by applying to the soil prior to emergence of weeds therefrom or to the plant surfaces subsequent to emergence from the soil, a herbicidally effective amount of a compound of this invention. It is, of course, to be understood that the term "a compound of this invention" also includes mixtures of such compounds or a formulation containing a compound or mixture of compounds of this invention.

The term "herbicidally effective amount" is that amount of a compound of this invention required to so injure or damage weeds such that the weeds are incapable of recovering following application while not causing substantial injury to any valuable crop amongst which the weeds might be growing. The quantity of compound of this invention applied in order to exhibit a satisfactory herbicidal effect may vary over a wide range and depends on a variety of factors, such as, for example, hardiness of a particular weed species, extent of weed infestation, climatic conditions, soil conditions, method of application, and the like. Typically, as little as one or less pound or acre of a compound of this invention would be expected to provide satisfactory weed control, although in some instances application rates in excess of one pound per acre, e.g., up to 5 or more pounds per acre might be required. Of course, the efficacy of a particular compound against a particular weed species may readily be determined by routine laboratory or field testing in a manner well known to the art. It is expected that satisfactory weed control can be had at a rate of application in the range of 0.1 to 1.0 pound per acre.

Of course, a compound of this invention can be formulated according to routine methods with any of several known and commonly used herbicidal diluents, adjuvants and carriers. The formulations can contain liquid carriers and adjuvants such as organic solvents, as well as emulsifiers, stabilizers, dispersants, suspending agents, spreaders, penetrants, wetting agents and the like. Typical carriers utilized in dry formulations include clay, talc, diatomaceous earth, silica and the like. Preferred formulations are those in the form of wettable powders, flowables, dispersible granulates or aqueous emulsifiable concentrates which can be diluted with water at the site of application. Also, dry formulations such as granules, dusts, and the like, may be used.

When, desired, a compound of this invention can be applied in combination with other herbicidal agents in an agents in an effort to achieve even broader vegetative control. Typical herbicides which can be conveniently combined with Formula I compound include atrazine, hexazinone, metribuzin, ametryn, cyanazine, cyprazine, prometon, prometryn, propazine, simazine, terbutryn, propham, alachlor, acifluorfen, bentazon, metalachlor and N,N-dialkyl thiocarbamates such as EPTC, butylate or venolate. These, as well as other herbicides described, for example, in the *Herbicide Handbook of the Weed Science Society of America*, may be used in combination with a compound or compounds of the invention. Typically such formulations will contain from about 5 to about 95 percent by weight of a compound of this invention.

The herbicidally formulations contemplated herein can be applied by an of several method known to the art. Generally, the formulation will be surfaced applied as an aqueous spray. Such application can be carried about by conventional ground equipment, or if desired, the sprays can be aerially applied. Soil incorporation of such surface applied herbicides is accomplished by natural leaching, and is of course facilitated by natural rainfall and melting snow. If desired, however, the herbicides can be incorporated into the soil by conventional tillage means.

Compounds of this invention are believed effective for emergence of postemergence control of a wide variety of broadleaf and grassy weeds. Typical of the various species of vegetative growth that may be controlled, combated, or eliminated are, for example, annuals such as pigweed, lambsquarters, foxtail, crabgrass, wild mustard, field pennycress, ryegrass, goose grass, chickweed, wild oats, velvetleaf, purslane, barnyardgrass, smartweed, knotweed, cocklebur, kochia, medic, ragweed, hemp nettle, spurrey, pondweed, carpetweed, morningglory, ducksalad, cheatgrass, fall panicum, jimsonweed, witchgrass, watergrass, wild turnip, and similar annual grasses and weeds. Biennials that may be controlled include wild barley, campion, burdock, bull thistle, roundleaved mallow, purple star thistle, and the like. Also controlled by the compounds of this invention are perennials such as quackgrass, Johnsongrass, Canada thistle, curley dock, field chickweed, dandelion, Russian knapweed aster, horsetail, ironweed, sesbania, cattail, wintercress, horsenettle, nutsedge, milkweed, sicklepod, and the like.

The compounds prepared as described in the Examples were individually tested for herbicidal efficacy against a variety of broadleaf and grassy weed species, under controlled laboratory conditions of light, humidity and temperature. Solvent solutions of said compounds were applied, both preemergence and postemergence, to test flats containing the various weed species, and herbicidal efficacy was evaluated vis a vis an untreated control, by periodic visual inspection after application of the compounds. The compounds exhibited excellent herbicidal efficacy both preemergence and postemergence at an application rate as low as 0.1 pound per acre. Also the compounds exhibit outstanding monocot crop tolerance. For example, the compound of Example III, when applied postemergence to corn at a rate of 5.0 pounds per acre, caused no discernable injury to the corn.

Although the invention has been described in considerable detail by the foregoing, it is to be understood that many variations may be made therein by those skilled in the art without departing from the spirit and scope thereof as defined by the appended claims.

I claim:

1. A compound of the formula:

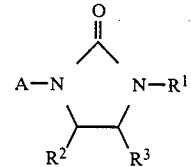

wherein
A is

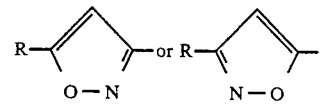

wherein
R is up to $C_6$ alkyl, haloalkyl or cycloakyl, up to $C_5$ alkenyl or alkynyl; $-R^4-O-R^5$ or $-R^4-S-R^5$ wherein $R^4$ is up to $C_6$ alkylene and $R^5$ is up to $C_6$ alkyl or phenyl or benzyl;

$R^1$ is up to $C_3$ alkyl or allyl;

$R^2$ and $R^3$ are selected from hydrogen, hydroxy or $-NR^6R^7$ with the proviso that one of $R^2$ or $R^3$ must be $-NR^6R^7$, wherein $R^6$ is selected from hydrogen or up to $C_6$ alkyl or haloalkyl; and $R^7$ is

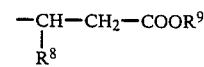

wherein
$R^8$ is selected from hydrogen, up to $C_6$ alkyl or haloalkyl, phenyl or benzyl and $R^9$ is selected from alkali metal, hydrogen, up to $C_6$ alkyl, haloalkyl or alkoxyalkyl, or phenyl.

2. A compound of claim 1 of the formula:

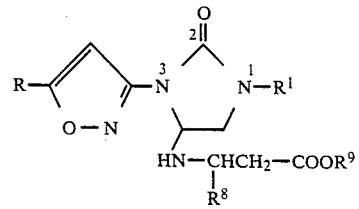

wherein R and $R^1$ are $C_1$ to $C_3$ alkyl, $R^9$ is hydrogen or $C_1$ to $C_3$ alkyl.

3. A compound of claim 2 wherein R is t-butyl and $R^1$ is methyl.

4. A compound of claim 3 wherein $R^8$ and $R^9$ are each hydrogen.

5. A herbicidal composition containing an inert carrier and a herbicidally effective amount of a compound or mixture of compounds defined in claim 1.

6. The method of controlling the growth of weeds wherein a herbicidally effective amount of herbicide is applied to a growth medium prior to emergence of weeds therefrom or to the weeds subsequent to emergence from the growth medium wherein the improvement resides in using as the herbicide a compound or mixture of compounds as defined in claim 1.

* * * * *